United States Patent
Lurie et al.

(10) Patent No.: US 6,425,393 B1
(45) Date of Patent: Jul. 30, 2002

(54) AUTOMATIC VARIABLE POSITIVE EXPIRATORY PRESSURE VALVE AND METHODS

(75) Inventors: Keith G. Lurie, Minneapolis, MN (US); Wolfgang Voelckel, Telfs (AT); Todd Zielinski, Minneapolis, MN (US)

(73) Assignee: CPRX LLC, Minneapolis, MN (US)

( * ) Notice: Subject to any disclaimer, the term of this patent is extended or adjusted under 35 U.S.C. 154(b) by 0 days.

(21) Appl. No.: 09/386,868

(22) Filed: Aug. 31, 1999

Related U.S. Application Data

(63) Continuation-in-part of application No. 08/950,702, filed on Oct. 15, 1997, now Pat. No. 6,062,219, which is a continuation-in-part of application No. 08/403,009, filed on Mar. 10, 1995, now Pat. No. 5,692,498, which is a continuation-in-part of application No. 08/149,240, filed on Nov. 9, 1993, now Pat. No. 5,551,420.

(51) Int. Cl.[7] .................................................. A62B 7/00
(52) U.S. Cl. .............................. 128/200.24; 128/202.28
(58) Field of Search ....................... 128/205.24, 205.13, 128/202.28, 200.24, 202.29, 203.11, 204.18, 205.19, 205.14, 205.15, 205.16, 207.14, 207.15, 911, 912

(56) References Cited

U.S. PATENT DOCUMENTS

| | | | |
|---|---|---|---|
| 2,774,121 A | 12/1956 | Halliburton ................... | 128/29 |
| 3,191,596 A | 6/1965 | Bird et al. ..................... | 128/29 |
| 3,662,751 A | 5/1972 | Barkalow et al. ......... | 128/145.8 |
| 3,669,108 A | 6/1972 | Sundblom et al. ........ | 128/145.8 |
| 3,794,043 A | 2/1974 | McGinnis ............ | 128/349 BV |

(List continued on next page.)

FOREIGN PATENT DOCUMENTS

| | | |
|---|---|---|
| CA | 668771 | 8/1963 |
| CA | 2077608 | 3/1993 |
| EP | 0 029 352 | 5/1981 |
| EP | 0367 285 A2 | 5/1990 |
| EP | 0 411 714 A1 | 2/1991 |
| EP | 0 509 773 A1 | 10/1992 |
| GB | 1 465 127 | 11/1974 |
| GB | 2 139 099 A | 11/1984 |
| WO | WO 90/05518 | 5/1990 |
| WO | WO 93/21982 | 11/1993 |
| WO | WO 94/26229 | 11/1994 |
| WO | WO 95/13108 | 5/1995 |
| WO | WO 95/28193 | 10/1995 |
| WO | WO 96/28215 | 9/1996 |

OTHER PUBLICATIONS

US 5,584,866, 12/1996, Kroll et al. (withdrawn)
Geddes, L.A., "Electrically Produced Artifical Ventilation," *Medical Instrumentation* 22(5): 263–271 (1988).
Glenn, William W.L., et al., "Twenty Years of Experience in Phrenic Nerve Stimulation to Pace the Diaphragm," *Pace* 9: 780–784 (Nov./Dec. 1986, Part I).
Kotze, P.L. et al., "Diaphragm Pacing in the Treatment of Ventilatory Failure," *Sant. Deel* 68:223–224 (Aug. 17, 1995).
Geddes, L.A. et al., "Inspiration Produced by Bilateral Electromagnetic, Cervical Phrenic Nerve Stimulation in Man," *IEEE Transactions on Biomedical Engineering* 38(9): 1047–1048 (Oct. 1991).

(List continued on next page.)

*Primary Examiner*—John G. Weiss
*Assistant Examiner*—Teena Mitchell
(74) *Attorney, Agent, or Firm*—Townsend and Townsend and Crew LLP

(57) ABSTRACT

The invention provides exemplary methods and valves used to alter a person's breathing. In one method, an exit valve is interfaced with a person's airway. The exit valve is configured such that respiratory gases are prevented from exiting the person's lungs when the exit valve is closed and are permitted to exit the person's lungs when the exit valve is opened. The exit valve is configured to open when a valve actuating pressure is met or exceeded. In a further step, the valve actuating pressure is varied over time.

16 Claims, 8 Drawing Sheets

U.S. PATENT DOCUMENTS

| | | | |
|---|---|---|---|
| 3,815,606 A | 6/1974 | Mazal | 128/351 |
| 3,834,383 A | 9/1974 | Weigl et al. | 128/145.8 |
| 4,041,943 A | 8/1977 | Miller | 128/145.8 |
| 4,077,404 A | 3/1978 | Elam | 128/145.8 |
| 4,166,458 A | 9/1979 | Harrigan | 128/24 |
| 4,226,233 A | 10/1980 | Kritzer | 128/205.13 |
| 4,259,951 A | 4/1981 | Chernack et al. | 128/200.14 |
| 4,298,023 A | 11/1981 | McGinnis | 137/529 |
| 4,316,458 A | 2/1982 | Hammerton-Fraser | 128/205.24 |
| 4,397,306 A | 8/1983 | Weisfeldt et al. | 128/28 |
| 4,446,864 A | 5/1984 | Watson et al. | 128/28 |
| 4,449,526 A | 5/1984 | Elam | 128/206.21 |
| 4,533,137 A | 8/1985 | Sonne | 272/99 |
| 4,601,465 A | 7/1986 | Roy | 272/99 |
| 4,809,683 A | 3/1989 | Hanson | 128/28 |
| 4,827,935 A | 5/1989 | Geddes et al. | 128/28 |
| 4,881,527 A | 11/1989 | Lerman | 128/30.2 |
| 4,928,674 A | 5/1990 | Halperin et al. | 128/30.2 |
| 5,014,698 A | 5/1991 | Cohen | 128/419 |
| 5,050,593 A | 9/1991 | Poon | 128/204.23 |
| 5,109,840 A * | 5/1992 | Daleiden | 128/205.13 |
| 5,163,424 A | 11/1992 | Kohnke | 128/205.13 |
| 5,184,620 A | 2/1993 | Cudahy et al. | 128/639 |
| 5,193,544 A | 3/1993 | Jaffe | 128/634 |
| 5,235,970 A | 8/1993 | Augustine | 128/200.26 |
| 5,301,667 A | 4/1994 | McGrail et al. | 128/205.14 |
| 5,305,743 A | 4/1994 | Brain | 128/207.15 |
| 5,355,879 A | 10/1994 | Brain | 128/207.15 |
| 5,359,998 A | 11/1994 | Lloyd | 128/203.11 |
| 5,392,774 A | 2/1995 | Sato | 128/207.15 |
| 5,454,779 A | 10/1995 | Lurie et al. | 601/43 |
| 5,492,116 A | 2/1996 | Scarberry et al. | 128/206.34 |
| 5,496,257 A | 3/1996 | Kelly | 601/41 |
| 5,517,986 A | 5/1996 | Starr et al. | 128/206.24 |
| 5,551,420 A | 9/1996 | Lurie et al. | 128/205.13 |
| 5,645,522 A | 7/1997 | Lurie et al. | 601/43 |
| 5,692,498 A | 12/1997 | Lurie et al. | 128/205.24 |
| 5,730,122 A | 3/1998 | Lurie | 128/207.12 |
| 5,735,876 A | 4/1998 | Kroll et al. | 607/5 |
| 5,738,637 A | 4/1998 | Kelly et al. | 601/41 |
| 5,782,883 A | 7/1998 | Kroll et al. | 607/14 |
| 5,814,086 A | 9/1998 | Hirschberg et al. | 607/14 |
| 6,062,219 A * | 5/2000 | Lurie et al. | 128/205.24 |

OTHER PUBLICATIONS

Geddes, L.A. et al., "Optimum Stimulus Frequency for Contracting the Inspiratory Muscles with chest Surface Electrodes to Produce Artifical respiration," *Annals of Biomedical Engineering* 18:103–108 (1990).

Laghi, Franco et al., "Comparison of Magnetic and Electrical Phrenic Nerve Stimulation in assessment of Diaphragmatic Contractility," *American Physiological society*, pp. 1731–1742 (1996).

Glenn, William W.L. et al., "Diaphragm Pacing by Electrical Stimulation of the Phrenic Nerve," *Neurosurgery* 17(6): 974–984 (1985).

Dupuis, Yvon G., "Ventilators Theory and Clinical Application," Mosby Company 1986.

Ambu International A/S, "Directions for use fo Ambu CardioPump".

Cohen, Todd J. et al., "Active Compression–Decompression Resuscitation: A novel method of Cardopulmonary Resuscitation," Department of Medicine and the Cardiovascular Research Institute, UC San Francisco, (1992).

Cohen, Todd J. et al., "Active Compression–Decompression: A new method of cardiopulmonary Resuscitation," *JAMA* 267(21): 2916–2923 (Jun. 3, 1992).

Lindner, Karl H. et al., "Effects of Active compression–Decompression Resuscitation on Myocardial and Cerebral Blood Flow in Pigs" Department of Anesthesiology and Critical Care Medicine, University of Ulm, Germany (Oct. 7, 1993).

Lurie, Keith G. et al., "Regulated to Death: The Matter of Informed Consent for Human Experimentation in Emergency Resuscitation Research," Cardiac Arrhythmia Center at the University of Minnesota 18:1443–1447 (Jul. 1995).

* cited by examiner

AUTOMATIC VARIABLE POSITIVE EXPIRATORY PRESSURE VALVE AND METHODS

CROSS REFERENCE TO RELATED APPLICATIONS

This application is a continuation-in-part application of U.S. application Ser. No. 08/950,702, filed Oct. 15, 1997 (now U.S. Pat. No. 6,062,219), which is a continuation-in-part of U.S. Pat. application Ser. No. 08/403,009, filed Mar. 10, 1995 (now U.S. Pat. No. 5,692,498), which is a continuation-in-part of U.S. Pat. application Ser. No. 08/149,240, filed Nov. 9, 1993 (now U.S. Pat. No. 5,551,420).

BACKGROUND OF THE INVENTION

This invention relates generally to the field of respiratory gases, and in particular, to the management of respiratory gases. More specifically, the invention relates to the use of positive expiratory pressures, or PEP.

Medical research has shown that PEP improves gas exchange in the lungs under certain conditions. To create a PEP within a patient, a variety of PEP valves have been constructed to prevent respiratory gases from exiting the lungs. For example, some compressible bags, such as an AMBU bag, commercially available from AMBU International, Denmark, incorporate a PEP valve. This type of compressible bag is coupled to a facial mask that is placed over a patient's mouth and nose. The compressible bag is compressed to deliver air to the patient's lungs. When the patient exhales, the PEP valve creates a PEP within the patient.

One specific application of PEP is in connection with cardiopulmonary resuscitation (CPR) procedures. For example, U.S. Pat. Nos. 5,551,420 and 5,692,498, the disclosures of which are herein incorporated by reference, describe various PEP valves that may be used in connection with CPR procedures.

CPR procedures typically involve a compression phase where the patient's chest is actively compressed, and a decompression phase where the patient's chest is allowed to return to its decompressed state, either by its own resilience or through techniques employed to actively lift the chest. Recently, a number of devices have been developed to enhance venous blood return during the decompression phase of CPR. These devices augment venous return by either decreasing intrathoracic pressure during the decompression phase, thereby drawing venous blood into the thorax, or by pushing venous blood into the thorax by actively compressing the abdominal cavity. The use of PEP during CPR has been suggested as one way to force this blood out of the thorax. For instance, as recited in U.S. Pat. No. 5,692,498, use of a "pressure-responsive expiration valve during decompression may further increase intrathoracic pressure and thereby force more blood out of the thorax."

Hence, this invention relates generally to various techniques involving the use of PEP. The invention also relates to various types of valves used to produce PEP in a patient. In one specific aspect, the invention relates to the use of PEP when performing CPR procedures.

SUMMARY OF THE INVENTION

In one embodiment of the invention, a method is provided for altering a person's breathing. According to the method, an exit valve is interfaced with the person's airway. The exit valve is configured such that respiratory gases are prevented from exiting the person's lungs when the exit valve is closed. Respiratory gases are permitted to exit the person's lungs when the exit valve is opened. Further, the exit valve is configured to open when a valve actuating pressure is met or exceeded. In use, the valve actuating pressure is varied over time. In this way, a positive expiratory pressure (PEP) is provided within the person. Further, the PEP is varied over time as the valve actuating pressure is varied. For example, the valve actuating pressure may be increased over time so that the pressure of the respiratory gases held within the patient is also increased over time.

In one particular aspect, the method is used in connection with a cardiopulmonary resuscitation (CPR) procedure where the patient's chest is periodically compressed while the exit valve is interfaced with the person's airway. In this way, as the patient's chest is compressed, respiratory gases are forced against the exit valve. When the pressure of the respiratory gases meets or exceeds the actuating pressure, the valve is opened to allow the respiratory gases to exit the patient's lungs. Optionally, the person's chest may be compressed with a compression mechanism.

When used in association with a CPR procedure, the valve actuating pressure may be varied within a range from about 0 cm $H_2O$ to about 20 cm $H_2O$, and more preferably in the range from about 2.5 cm $H_2O$ to about 10 cm $H_2O$. Further, the valve actuating pressure may be varied over a time period in the range from about 5 minutes to about 30 minutes. In the event that cardiac function is successfully obtained, the exit valve may be removed from the patient's airway.

In another particular aspect, the person's chest may be actively lifted in an alternating manner with chest compressions. In an alternative aspect, the patient's abdomen may be periodically compressed in an alternating manner with chest compressions. By actively lifting the person's chest or compressing the person's abdomen, more venous blood is forced into the thorax. In still another alternative aspect, an impedance valve may be interfaced with the patient's airway. The impedance valve may be configured to open to permit respiratory gases to flow to the person's lungs once a threshold negative intrathoracic pressure is met or exceeded. Such an impedance valve may be employed to create a greater vacuum effect during the decompression phase of CPR to increase coronary perfusion pressure and myocardial blood flow. Use of the exit valve in combination with the impedance valve and/or techniques where the person's chest is actively lifted or the person's abdomen is compressed improves oxygenation while maintaining and/or increasing coronary perfusion pressure, thereby increasing the efficiency of the CPR procedure. Conveniently, the impedance valve and the exit valve may be combined into a single device.

In another embodiment, the invention provides an exit valve that is configured to open when an actuating pressure is met or exceeded to permit respiratory gases to exit the person's lungs. An adjustment mechanism is provided to vary the actuating pressure of the exit valve over time, or in a cyclical fashion after one or more chest compressions, with a cycle being a chest compression phase followed by a decompression phase.

In one specific aspect, the actuating pressure of the exit valve is configured to be in the range from about 0 cm $H_2O$ to about 20 cm $H_2O$, and more preferably in the range from about 2.5 cm $H_2O$ to about 10 cm $H_2O$.

In one particular aspect, the exit valve comprises a valve housing that defines an airway. A valve member is disposed in the housing and is movable between a closed position that prevents the passage of respiratory gases through the airway and an open position where respiratory gases are permitted to flow through the airway. The valve member is configured to remain in the closed position until a pressure acting against the valve member meets or exceeds the actuating pressure. At this point in time, the valve member moves to the open position, allowing expiratory gases to be released.

In one aspect, a biasing mechanism is provided to apply a force against the valve member to bias the valve member in the closed position. With this configuration, the mechanism to vary the actuating pressure may comprise a system to vary the applied force supplied by the biasing mechanism. As one example, the system may comprise a lead screw to move the biasing mechanism over time. In one aspect, the biasing mechanism may comprise a spring. In this way, as the lead screw is turned, the spring is compressed over time, thereby applying a greater force against the valve member. In another aspect, the biasing mechanism may comprise a pair of spaced apart, opposing pole magnets. As the pole magnets are moved closer to each other over time, the force acting against the valve member is increased. Conversely, as the pole magnets are moved further away from each other, the force against the biasing member is lessened.

In another aspect, a knob is provided to manually operate the lead screw. Alternatively, a spring loaded mechanism may be provided to automatically turn the lead screw over time. As another example, the system may comprise a linear actuator to move the biasing member. The linear actuator may be programmed so that it automatically moves the biasing member a predetermined amount over a predetermined time.

In one particular aspect, the housing defines an intake port and the valve member is disposed across the intake port when in the closed position. The housing also defines an exhaust port downstream of the intake port to exhaust respiratory gases once the valve member moves from the closed position. In yet another aspect, the valve member may comprise a float that is disposed within a chamber. With this arrangement, the biasing mechanism may comprise a pressure source to vary the pressure within the chamber.

The exit valve may optionally be included as part of a system for controlling the flow of respiratory gases. For example, the system may also include an impedance valve that is configured to open to permit respiratory gases to flow to the person's lungs once a threshold negative intrathoracic pressure is met or exceeded. The exit valve may be a valve that is separate from the impedance valve or may conveniently be incorporated into the impedance valve. The system may also include various mechanisms for assisting in a CPR procedure. For example, the system may include a compression mechanism for compressing the person's chest. A lifting member may also be provided that is adapted to be secured to the person's chest to actively lift the person's chest.

In another particular aspect, the system may include an interface member to which the valve is coupled. In this way, the interface member may be coupled to a person's airway to place the exit valve in communication with the airway. In another alternative, the system may include a compressible bag, with the exit valve being coupled to the compressible bag.

DESCRIPTION OF THE SPECIFIC EMBODIMENTS

Figure 1:
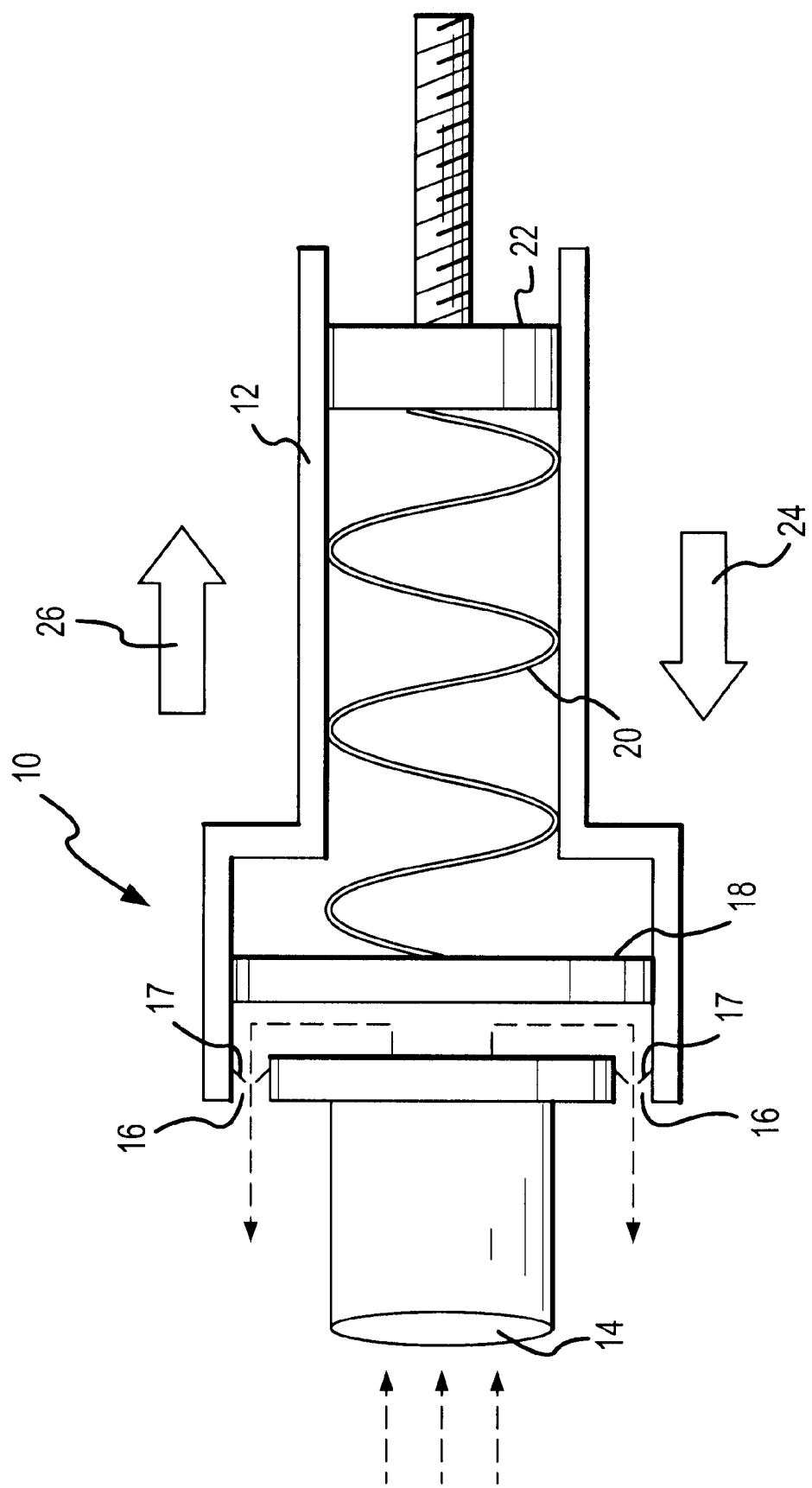
FIG. 1 is a schematic view of one embodiment of a valve having a variable actuating pressure according to the invention.

The invention provides various techniques for altering a person's ventilation. According to one aspect of the invention, respiratory gases are prevented from escaping from a person's lungs for at least a portion of a ventilation or breathing cycle. The respiratory gases may be prevented from exiting the patient's lungs during the patient's own exhalation efforts or when attempting to actively force the respiratory gases out of the lungs, e.g., when the person's chest is compressed. The respiratory gases may be prevented from exiting the person's lungs until the respiratory gases within the person reach or exceed a threshold pressure. At this point in time, the respiratory gases are allowed to escape from the patient's lungs. In one particular aspect of the method, this threshold pressure is varied over time. In this way, the PEP created within the person is varied over time.

One particular use of such a technique is in connection with various CPR procedures. Examples of CPR procedures that may find use with such techniques include standard CPR in combination with active compression/decompression techniques (ACD), the use of an impedance valve which prevents respiratory gases from flowing to the patient's lungs until a negative intrathoracic pressure is met or exceeded as described generally in U.S. Pat. Nos. 5,551, 420 and 5,692,498, previously incorporated herein by reference, Life Stick CPR, interposed abdominal counter-pulsation CPR, respiratory muscular stimulation CPR as described generally in copending U.S. application Ser. Nos. 09/095,916, filed Jun. 11, 1998; 09/197,286, filed Nov. 20, 1998; and 09/315,396, filed May 20, 1999 (Attorney Docket No. 16354-32-2), and the like, as well as various combinations thereof. The complete disclosures of all the above references are herein incorporated by reference.

Depending on the particular CPR procedure, the effectiveness of successfully resuscitating a person may depend on factors such as the changing nature of lung fluids during a procedure, the changing nature of the backlog of pulmonary fluids during a procedure, and lung atelectasis. For example, some CPR procedures may enhance the occurrence of atelectasis, thereby affecting lung function and decreasing oxygenation. Some CPR procedures may also have an adverse effect on coronary perfusion pressure, thereby decreasing the amount of myocardial blood flow. By providing PEP within a person during the compression phase of a CPR procedure, and by increasing the amount of PEP over time, oxygenation may be improved and/or the amount of coronary perfusion pressure may be maintained. In this way, increasing PEP over time during a CPR procedure may significantly increase the chances of successfully resuscitating a person.

Merely by way of example, techniques where PEP is varied over time may be used in association with CPR procedures where incoming respiratory gases are impeded from entering the lungs until a threshold negative intrathoracic pressure is overcome with ACD procedures, and with procedures involving a combination of impeding airflow and ACD. When utilizing a variable PEP with such procedures, the amount of venous blood pooling into the lungs is reduced, thereby increasing respiratory gas exchange and coronary perfusion pressures. More specifically, during the performance of such CPR procedures, the lungs may function as a passive conduit as blood is transferred from the right ventricle to the left ventricle. The use of the variable PEP techniques of the invention allows for an optimization of pulmonary blood flow and perfusion to further enhance the overall CPR efficacy. For instance, by increasing the amount of PEP over time, the PEP serves as a pneumatic pump by increasing bronchiolar pressures leading to less atelectasis and more efficient emptying of blood from the lungs. In this manner, PEP serves as a pneumatic pump each time the chest is compressed. Increasing the amount of PEP over time is particularly advantageous in that the lungs may become "leaky" over time. As the amount of PEP is increased over time, the efficiency of the pneumatic pump is maintained so that the lungs may more efficiently be emptied of blood. Importantly, the use of PEP is able to improve oxygenation during CPR without significantly affecting coronary perfusion pressure. For example, the increase of PEP over time may improve oxygenation due to alveolar recruitment without decreasing venous return during the decompression phase, thus maintaining stable hemodynamic conditions. Hence, the use of PEP is able to significantly increase the chances of successful resuscitation.

In one aspect of the invention, the PEP may varied between active ventilations. For example, just prior to ventilating the patient, the PEP may be varied so that the PEP is highest after the ventilation is delivered.

When performing CPR procedures, respiratory gases may be prevented from exiting the person's lungs during the compression phase for pressures in the range from about 0 cm $H_2O$ to about 20 cm $H_2O$, and more preferably in the range from about 2.5 cm $H_2O$ to about 10 cm $H_2O$. Conveniently, the amount of PEP may be incremented (or decreased) in segments in the range from about 1 cm $H_2O$ to about 2 cm $H_2O$. In one aspect, the amount of PEP is increased in the amount of 2.5 cm $H_2O$ to about 10 cm $H_2O$ over a time period in the range from about 2 minutes to about 40 minutes, and more preferably in the range from about 5 minutes to about 30 minutes. As previously mentioned, given the dynamic nature of the changes in pulmonary interstitial pressures over time, such increasing amounts of PEP over time may be employed to optimize the value of PEP during a CPR procedure.

To prevent respiratory gases from exiting a person's lungs, the invention may utilize a valve that is configured to open when a threshold pressure is met or exceeded. The threshold valve may include an adjustment mechanism to vary the actuating pressure over time. In one aspect, the valve may be incorporated into appropriate structure to allow the valve to be interfaced with the person's airway. For example, the valve may be incorporated into a facial mask, a laryngeal mask airway, an endotracheal tube, a mechanical ventilator, or other airway device so that respiratory gases are prevented from exiting the person's lungs until the valve is opened. Optionally, the exit valves of the invention may be incorporated into other systems associated with respiratory or CPR procedures. For example, the exit valve may be incorporated into a valve system including an inspiratory threshold valve that is configured to open when a threshold negative intrathoracic pressure is met or exceeded as described in U.S. Pat. Nos. 5,551,420 and 5,692,498, previously incorporated herein by reference. As another example, the exit valves of the invention may be integrated into a compressible bag that is squeezed to supply respiratory gases to a person. As still another alternative, the exit valve may be incorporated into a mechanical ventilator or other ventilation system.

Hence, the exit valves of the invention may be used as stand alone valves, or be include in a system having other valves, such an impedance threshold valve. Further, the exit valves of the invention may be used for both CPR and non-CPR procedures, such as for lung training, e.g. with athletes, or in situations involving pulmonary compromise, e.g., due to disease, heart failure, or the like. The exit valves may also be incorporated into bag ventilators, various types of masks, laryngeal mask airways, mechanical ventilators, and the like.

The exit valves of the invention may be configured in a variety of ways to permit the valve to open after a valve actuating pressure is met or exceeded. Further, a variety of schemes may be employed to vary the actuating pressure of the valve over time. As one example, the valve may include a valve member that is disposed across an airway. A biasing force may be provided against the valve member to hold the valve member across the opening until the actuating pressure exceeds the biasing force against the valve member. At this time, the valve member moves to permit respiratory gases to flow through the airway. Examples of biasing forces that may be employed to bias the valve member across the airway include spring forces, other mechanical forces, magnetic forces, electromagnetic forces, pneumatic forces, hydraulic forces, and the like. These forces may be varied over time, either manually or in an automated manner, so that the actuating pressure of the valve will also be varied over time.

Referring now to FIG. 1, one example of an exit valve 10 will be described. Exit valve 10 comprises a housing 12 having an inlet 14 and an outlet 16. An airway is defined between inlet 14 and outlet 16. Optionally, a fishmouth valve 17 may be placed over each outlet 16. Exit valve 10 further includes a valve member 18 that is biased across the airway by a spring 20. As shown in FIG. 1, expiratory gases from a patient have entered inlet 14 and overcome the spring force of spring 20 to move valve member 18 within housing 12 so that the expiratory gases are free to exit housing 12 through outlet 16. Once the expiratory gases fall below a threshold pressure, spring 20 will force valve member 18 forward to close outlet 16.

Exit valve 10 further includes a translation mechanism 22 that is translatable back and forth within housing 12. To increase the actuating force of exit valve 10, translation mechanism 22 is moved in the direction of arrow 24. Conversely, to decrease the actuating pressure of valve 10, translation mechanism 22 is moved in the direction of arrow 26. As the valve actuating pressure increases, the amount of PEP created within the person is increased. Conversely, when the actuating pressure of valve 10 is decreased, the amount of PEP within the patient is decreased.

A variety of schemes may be employed to translate translation mechanism 22. These may be manual in nature or automated. Merely by way of example, systems that may be employed to move translation mechanism 22 include solenoids, linear actuators, hydraulic cylinders, pistons, pneumatic cylinders, and the like. When automated, the systems may be connected to a controller (that may be programmable) to control the amount of translation and the rate of translation. Conveniently, a power supply may be coupled to the translation mechanism so that exit valve 10 may be configured to be portable.

Figure 2:
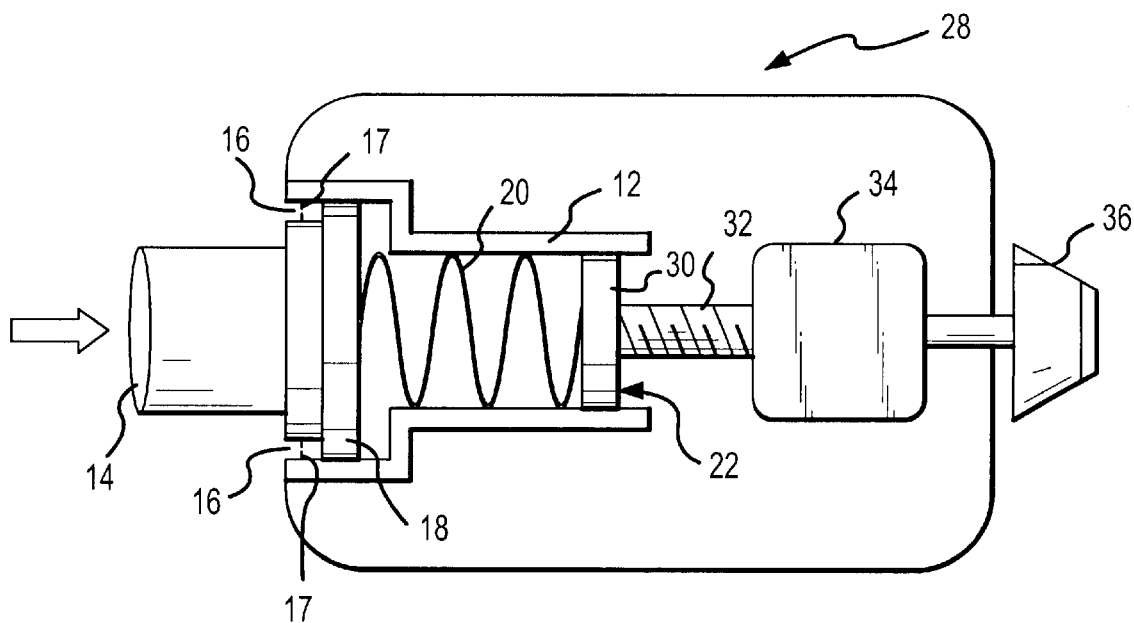
FIG. 2 is a schematic view of an alternative valve having a lead screw mechanism to vary the actuating pressure of the valve over time according to the invention.

Referring now to FIG. 2, an alternative embodiment of an exit valve 28 will be described. Exit valve 28 may conveniently utilize many of the same components of exit valve 10 in FIG. 1. As such, the elements in exit valve 28 which are similar to those of exit valve 10 will use the same reference numerals. In exit valve 28 of FIG. 2, translation mechanism 22 comprises a plunger 30 coupled to a lead screw 32. A gearbox 34 and a time setting knob 36 are employed to move lead screw 32 so that plunger 30 is translated through housing 12 to compress spring 20. Gearbox 34 may include one or more gears, one of which is coupled to the threads on lead screw 32 so that lead screw 32 is moved forward or backward upon turning of the gear. Gearbox 34 may also include a windup spring mechanism that is wound up by turning time setting knob 36. In this way, time setting knob 36 may be calibrated so that it may be turned a specified amount corresponding to the time required to unwind the spring mechanism within gear box 34. In this way, time setting knob may be employed to set a time for which the actuating pressure of valve 28 is increased. As the windup screwing mechanism in gearbox 34 unwinds, it turns the gear or gears within gearbox 34 to move lead screw 32 as previously described.

The actuation pressure of exit valve 28 may be varied by changing the spring constant of spring 20 and/or by changing the amount of translation of plunger 30. The rate at which the actuating pressure is varied may be changed by changing the size of the gears in gearbox 34 and/or the spring constant of the spring windup mechanism in gearbox 34. One reason for utilizing a mechanical windup mechanism is that exit valve 28 may be constructed in a relatively inexpensive manner so that it may be disposable following use. In this way, translation mechanism 22 will not need to be reset after each use. Rather, the entire exit valve may be disposed after a single use.

Figure 3:
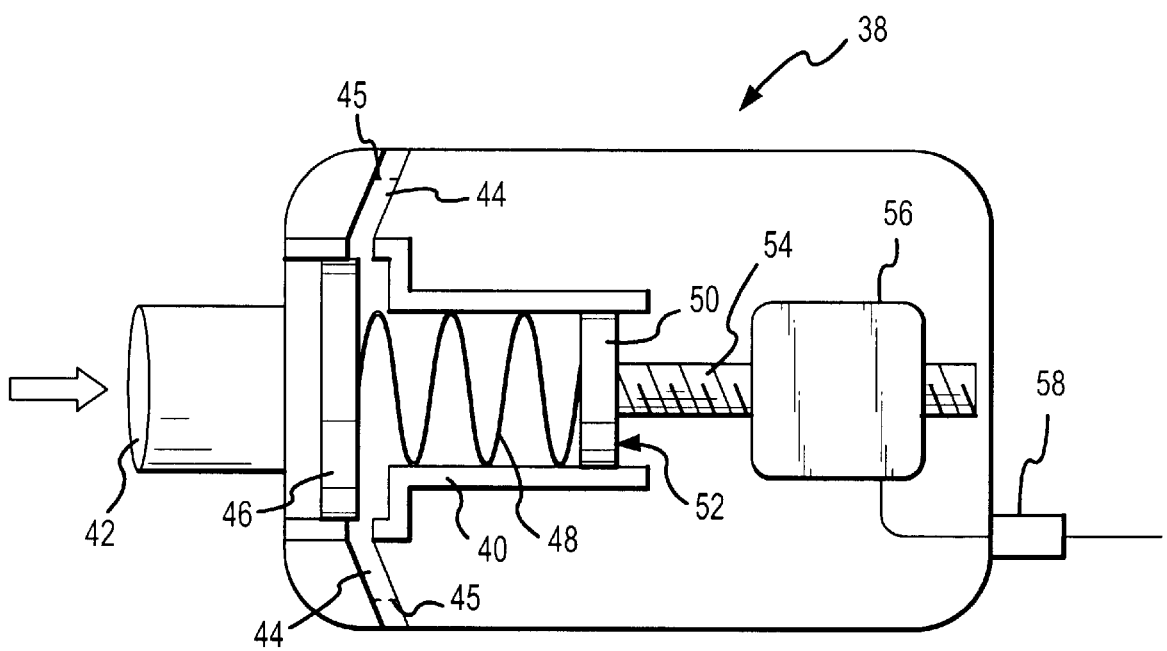
FIG. 3 is a schematic view of another alternative embodiment of a valve employing a linear actuator to vary the actuating pressure of the valve over time according to the invention.

Referring now to FIG. 3, another alternative embodiment of an exit valve 38 will be described. Exit valve 30 comprises a housing 40 having an inlet 42 and outlets 44. Optionally, a fishmouth valve 45 may be placed over each outlet 44. Disposed in housing 40 is a valve member 46 which is movable past outlets 44 when an actuating pressure is met or exceeded to allow respiratory gases entering through inlet 42 to exit outlets 44. A spring 48 is employed to bias valve member 46 in a closed position where respiratory gases are prevented from exiting outlets 44. The translation mechanism 50 is employed to vary the tension in spring 48 over time. Translation mechanism 50 comprises a plunger 52 and a lead screw 54. Movement of lead screw 54 is controlled by a linear actuator 56 which includes an electric motor and one or more gears to drive lead screw 54. Coupled to linear actuator 56 is an interface 58 which allows linear actuator 56 to be electronically coupled to actuator control circuity (not shown). In this way, appropriate hardware and/or software may be employed to control actuation of linear actuator 56. In this way, the rate at which plunger 52 is moved within housing 40 may be controlled to vary the rate at which the actuating pressure of exit valve 38 is varied over time.

Although not shown, it will be appreciated that linear actuator 56 of exit valve 38 may be employed in exit valve 28. In a similar manner, gear box 34 and time setting knob 36 of exit valve 28 may be employed in exit valve 38. In a similar manner, other translation mechanisms and/or actuators described herein may be used in connection with exit valves 28 and 38. Similarly, the various components of exit valves 28 and 38 may be used with the other exit valves described herein.

Figure 4:
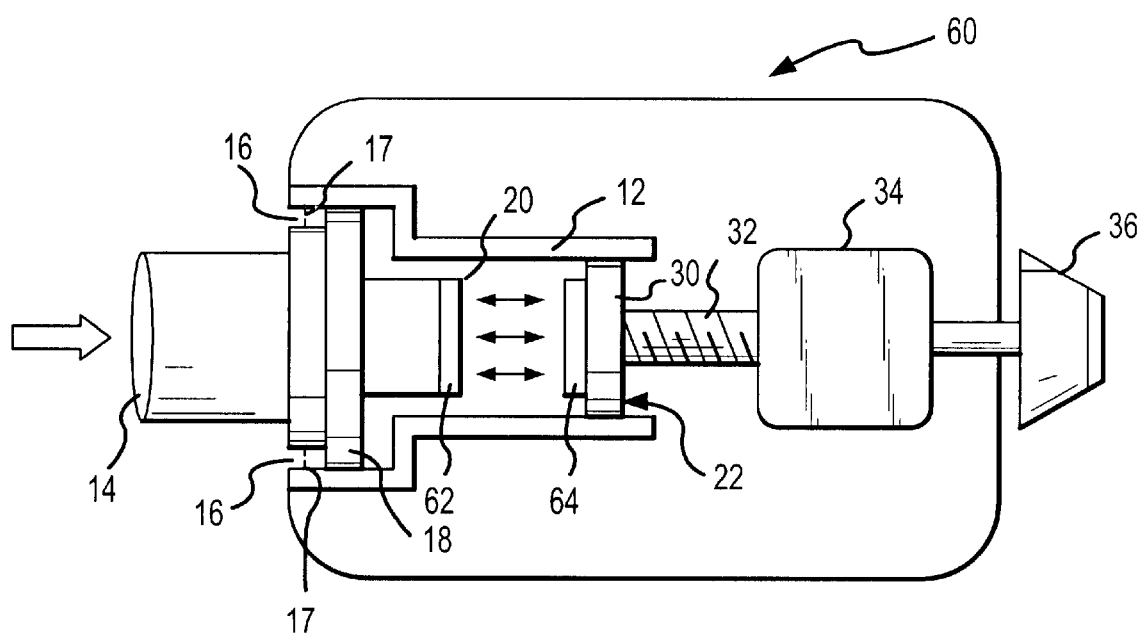
FIG. 4 is a schematic view of yet another alternative embodiment of a valve having a pair of spaced apart, opposing pole magnets to act as a biasing mechanism according to the invention.

Referring now to FIG. 4, still another embodiment of an exit valve 60 will be described. Exit valve 60 contains many components which are similar to those employed in exit valve 28. For convenience of illustration, the same components in exit valve 60 will be referred to with the same referenced numerals. Coupled to valve member 18 is a magnet 62 and coupled to plunger 30 is another magnet 64. Magnets 62 and 64 have opposite polarities so that they repel each other as they are brought in close proximity to each other. In this way, as plunger 30 moves magnet 64 closer to magnet 62, the actuating pressure of exit valve 60 is increased. Hence, one way to vary the valve actuating pressure is to vary the field strength of magnets 62 and 64. Another way to vary the valve actuating pressure is to control the distance between magnets 62 and 64.

Figure 5:
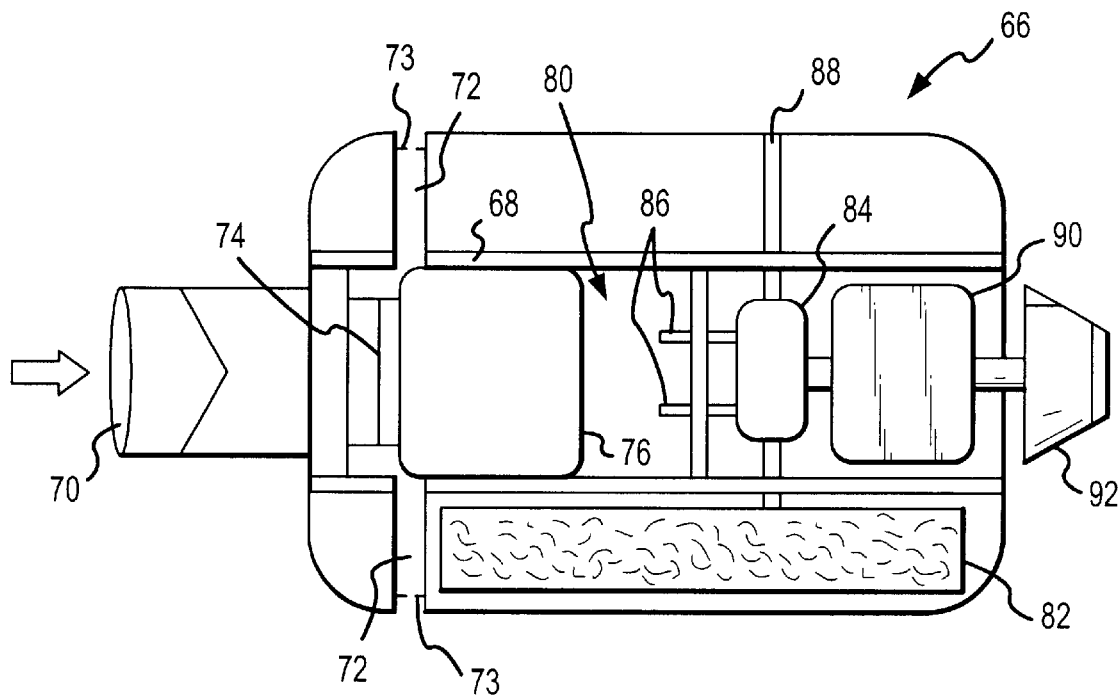
FIG. 5 is a schematic view of still yet another embodiment of a valve employing the use of a float and a pressure source to vary the actuating pressure of the valve over time according to the invention.

Shown in FIG. 5 is still another embodiment of an exit valve 66 which utilizes a pressurized gas to control actuation of the valve. Exit valve 66 comprises a housing 68 having an inlet 70 and outlets 72. Optionally, a fishmouth valve 73 may be placed over each outlet 72. Disposed between inlet 70 and outlets 72 is a port 74 having a seal, such as a rubber gasket. Movable against port 74 is a float control 76. Optionally disposed between inlets 70 and port 74 is a one way valve 78.

Exit valve 66 is configured such that when float control 76 is biased against port 74, respiratory gases are prevented from exiting outlet 72. As float control 76 is moved away from port 74, respiratory gases entering inlet 70 flow through port 74 and outlets 72.

Float control 76 is disposed within a sealed chamber 80. Pressurized gases may be supplied to sealed chamber 80 to bias float control 76 against port 74. Hence, the actuating pressure of exit valve 66 may be controlled by controlling the pressure within chamber 80 and/or the configuration of float control 76, e.g., its size.

To supply pressurized gases to chamber 80, exit valve 66 includes a pressure source 82 which may contain a wide variety of compressed gases, such as $CO_2$. In communication with pressure source 82 is a pressure control valve 84.

Extending from pressure control valve 84 is one or more pressure supply ports 86. Also extending from pressure control valve 84 is a pressure release port 88. In this way, pressure control valve 84 may be employed to control the pressure within chamber 80, with pressure release port 88 serving to bleed off any excess pressure.

A variety of actuation mechanisms may be employed to control the rate at which pressure control valve 84 regulates the pressure within chamber 80. For example, exit valve 66 may include a gear box 90 and time setting knob 92 which are similar to those employed with exit valve 28 of FIG. 2. Alternatively, any of the other actuating mechanisms described herein may be employed. In this manner, the actuating mechanism may be set to control the rate at which the pressure within chamber 80 is varied. In this way, the actuating pressure of exit valve 66 may be varied over time.

Figure 6:
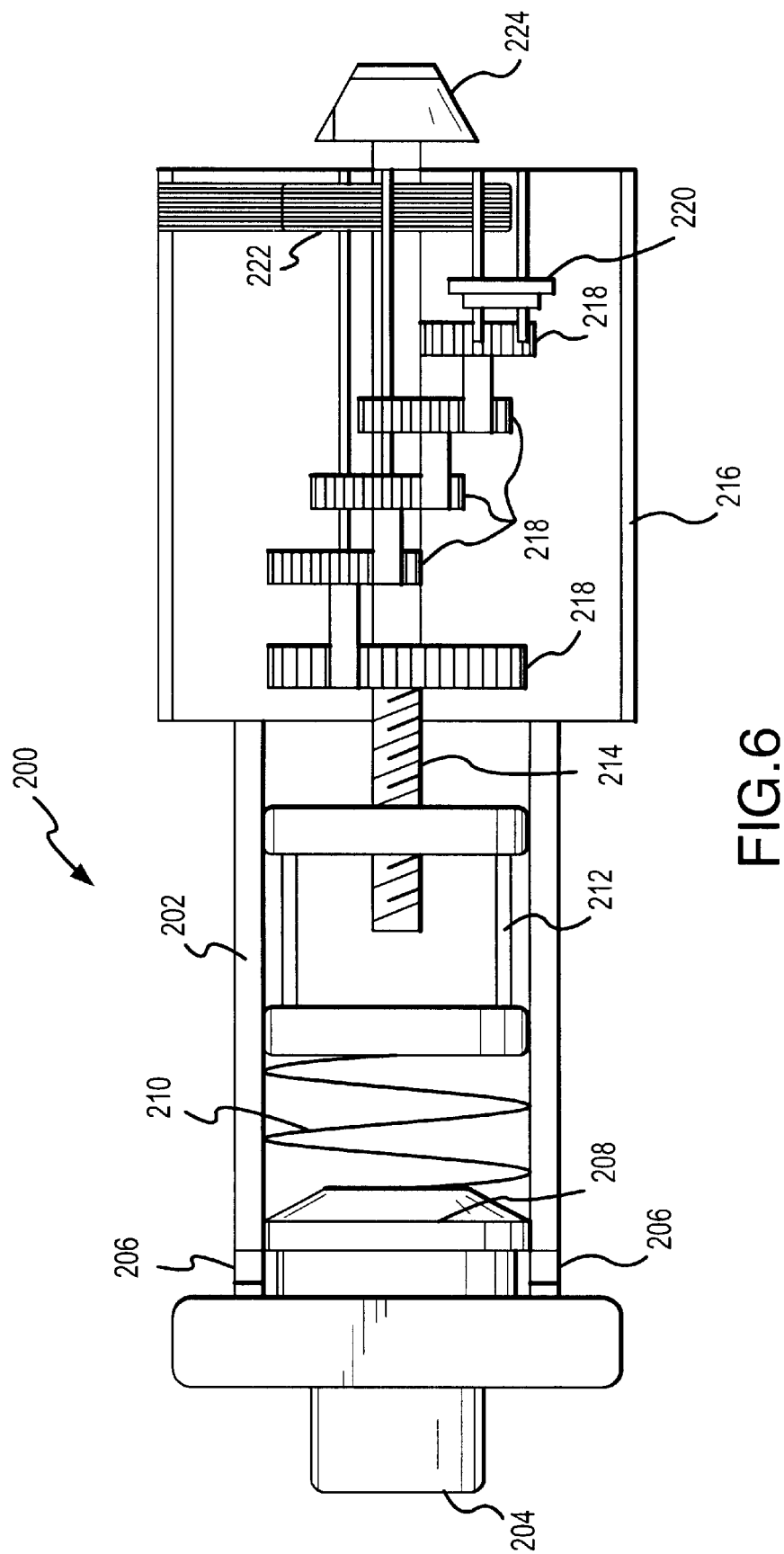
FIG. 6 is a schematic view of one embodiment of a valve having a set of timing gears to vary the actuating pressure of the valve over time according to the invention.

Referring now to FIG. 6, a further embodiment of an exit valve 200 will be described. Exit valve 200 comprises a housing 202 having an inlet 204 and outlets 206. Although not shown, outlets 206 may include a fishmouth valve similar to other embodiments described herein to prevent air from entering into housing 202 through outlets 206. Disposed in housing 202 is a valve member 208 that may conveniently comprise a diaphragm. Valve member 208 is movable past outlets 206 when an actuating pressure is met or exceeded to allow respiratory gases entering through inlet 204 to exit through outlets 206 in a manner similar to previous embodiments described herein. A spring 210 is employed to bias valve member 208 in a closed position to prevent respiratory gases from exiting outlets 206. A spring tension mechanism 212 is translatable within housing 202 and is used to vary the tension in spring 210 over time. A lead screw 214 is employed to translate the spring tension mechanism within housing 202.

Coupled to housing 202 is a spring loaded timing gear box 216 that is employed to rotate lead screw 214. Gear box 216 includes a plurality of timing gears 218, a spring recoil attenuator 220 and an energy recoil spring 222. A timing adjust knob 224 is also provided and may be rotated to wind up spring 222. Conveniently, knob 224 may be calibrated so that it may be turned a specified amount corresponding to the time required to unwind spring 222. In this manner, time setting knob 224 may be employed to set a time for which the actuating pressure of exit valve 200 is increased. As spring 222 unwinds, timing gears 218 are rotated to in turn rotate lead screw 214 and thus vary the actuating pressure. The number and size of gears 218 may be varied to control the rate of rotation of lead screw 214 and the size of spring 222. Spring recoil attenuator 220 is used to regulate the timing of release of spring tension.

Figure 7:
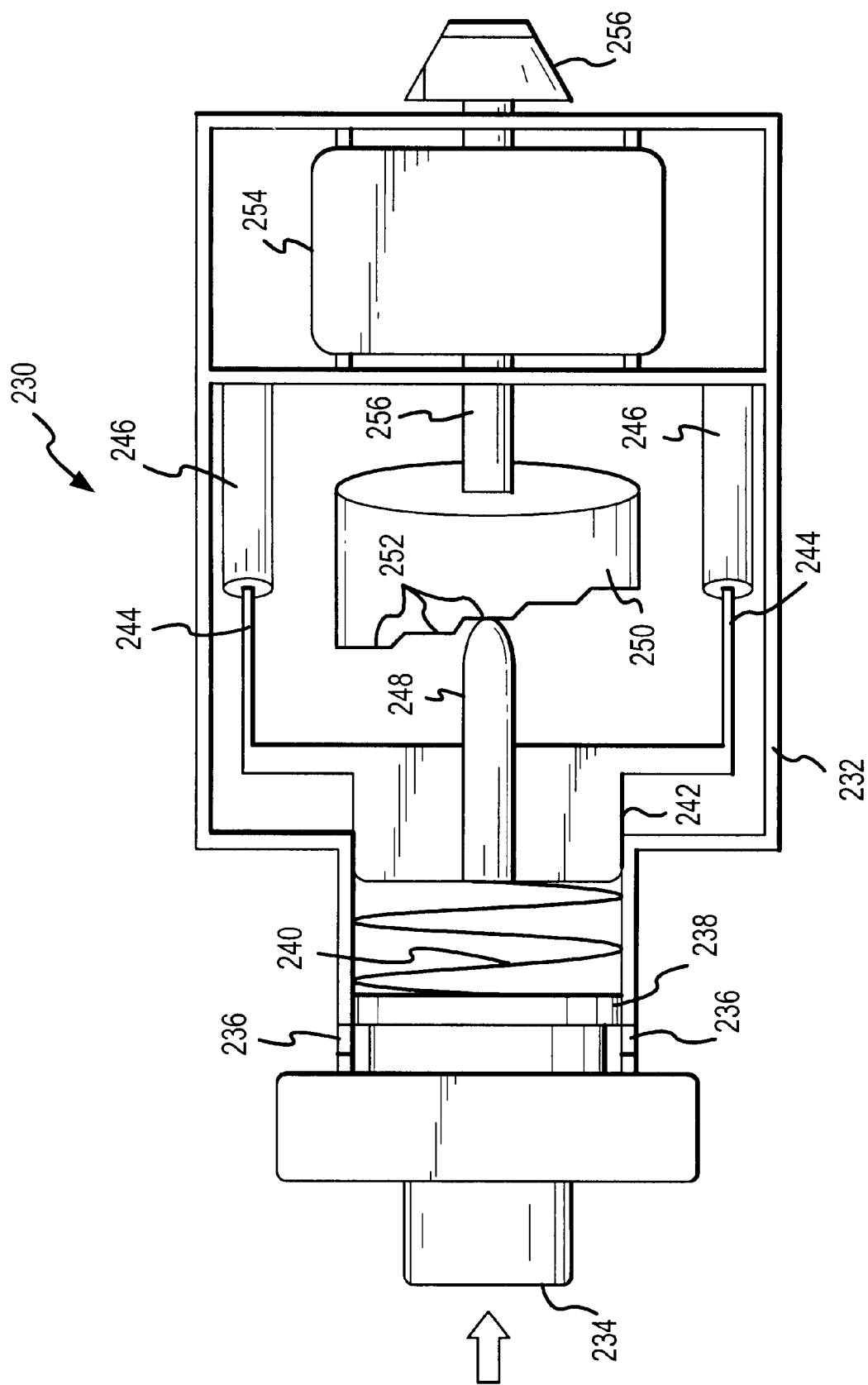
FIG. 7 is a schematic view of another embodiment of a valve having a rotating cam to vary the actuating pressure of the valve over time according to the invention.

FIG. 7 illustrates another embodiment of an exit valve 230 that may be employed to incrementally vary the PEP within a person in discrete steps. For instance, the actuating pressure of valve 230 may be increased over time in discrete steps, such as, for example, every 1 to 2 cm $H_2O$. Exit valve 230 comprises a housing 232 having an inlet 234 and outlets 236. Although not shown, outlets 236 may include a fishmouth valve similar to other embodiments described herein to prevent air from entering into housing 232 through outlets 236. Disposed in housing 232 is a valve member 238 that may conveniently comprise a diaphragm. Valve member 238 is movable past outlets 236 when an actuating pressure is met or exceeded to allow respiratory gases entering through inlet 234 to exit through outlets 236 in a manner similar to previous embodiments. A spring 240 is employed to bias valve member 238 in a closed position to prevent respiratory gases from exiting outlets 236. A spring tension mechanism 242 is translatable within housing 232 and is used to vary the tension in spring 240 over time.

Spring tension mechanism 242 includes a pair of guide rods 244 that are slidable within a corresponding pair of alignment cylinders 246 that are coupled to housing 232. Such an arrangement facilitates the smooth movement of spring tension mechanism 242 within housing 232. Spring tension mechanism 242 further includes a center rod 248 that is biased against a rotatable cam 250. Cam 250 includes a plurality of steps 252 that are employed to incrementally vary the tension within spring 240, thereby varying the actuating pressure of valve 230 in discrete steps.

A spring loaded timing gear box 254 is coupled to a shaft 256 that is employed to rotate cam 250. In this way, cam 250 may be rotated at a certain rate to incrementally increase the actuating pressure of valve 230 in discrete steps. The number of steps 252, the height of each step 252 and/or the rate of rotation of cam 250 may be varied depending on the desired rate of incremental pressure change and/or the number of pressure changes desired within a given cycle. A timing adjust knob 256 is also provided and may be rotated to wind up a spring within gear box 254. Conveniently, knob 256 may be calibrated so that it may be turned a specified amount corresponding to the time required to unwind the spring and thereby turn cam 250. In this manner, time setting knob 256 may be employed to set a time for which the actuating pressure of exit valve 230 is increased. Conveniently, gear box 254 may be constructed in a manner similar to the other gear boxes described herein.

Figure 8:
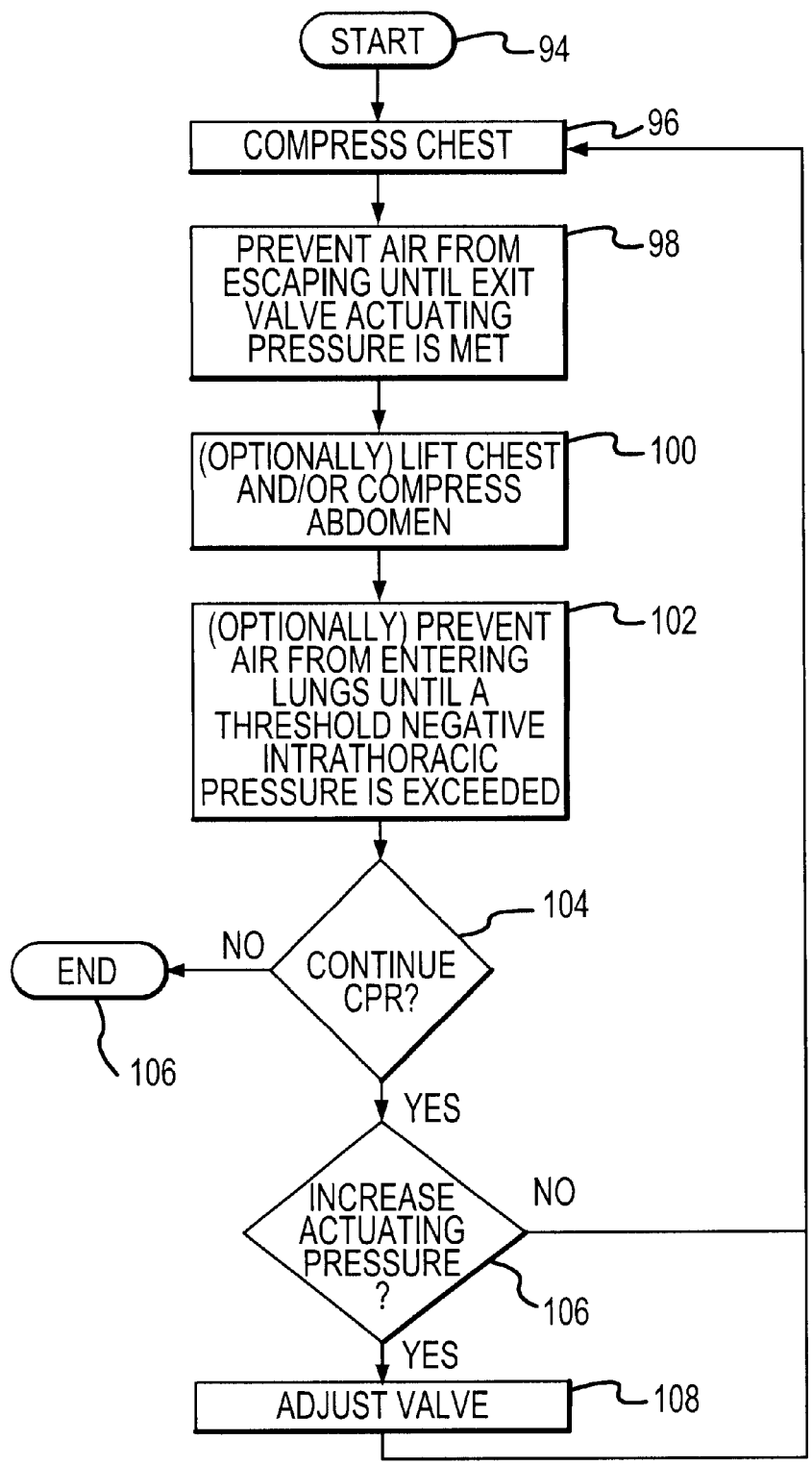
FIG. 8 is a flow chart illustrating one method for performing CPR using an exit valve to alter the person's PEP over time according to the invention.

Referring now to FIG. 8, one method for performing CPR using the techniques of the invention will be described. The procedure begins in step 94 and proceeds to step 96 where a person's chest is compressed. Typically, the person's chest will be compressed at a range in the rate from about 50 to about 100 compressions per minute. Optionally, a variety of chest compression enhancing techniques and/or equipment may be utilized during the compression step. For example, equipment such as an Ambu cardio pump, commercially available from Ambu International, an automated compression system, such as the Michigan Instruments Thumper device, and the like may be employed to compress the chest.

During at least some of the chest compressions, respiratory gases are prevented from escaping until an exit valve actuating pressure is met or exceeded as illustrated in step 98. When the actuating pressure is met or exceeded, the exit valve opens to allow gases from the person's lungs to exit. In this way, a significant amount of PEP is produced in the person to improve oxygenation without significantly affecting coronary perfusion pressure. In one aspect, respiratory gases are prevented from escaping during each chest compression. Alternatively, respiratory gases may be prevented from escaping once every 5 to about 10 chest compressions.

As illustrated in step 100, the person's chest may optionally be lifted during the decompression phase of CPR. In one alternative, the abdomen may optionally be compressed during the decompression phase. Such steps are optionally provided to force more venous blood back into the thorax during the decompression phase to permit more blood to be oxygenated and then forced back out of the person's chest. Optionally, other venous enhancing return techniques may be employed, including electrically stimulating the respiratory muscles, such as the diaphragm, as described generally in copending U.S. application Ser. No. 09/315,396, filed May 20, 1999 (Attorney Docket No. 16354-32-2), previously incorporated by reference.

As illustrated in step 102, the procedure may also optionally include the step of preventing respiratory gases from entering the lungs until a threshold negative intrathoracic pressure is met or exceeded. At such a point, respiratory gases are allowed to flow into the person's lungs as described generally in U.S. Pat. Nos. 5,551,420 and 5,692,498, previously incorporated by reference. The preventing techniques of step 98 may be particularly useful when preventing respiratory gases from entering the lungs as recited in step 102 by reducing the chances of atelectasis, thereby improving oxygenation without significantly affecting coronary perfusion pressure.

Still referring to FIG. 8, the process proceeds to step 104 to determine if CPR should be continued. If not, the process ends as shown in step 106. If it is desired to continue CPR, the procedure proceeds to step 106 to determine whether the exit valve actuating pressure should be increased. If not, CPR is continued by repeating steps 96–102. If the actuating is to be increased, the method proceeds to step 108 where the actuating pressure of the valve is adjusted and then CPR is continued. The actuating pressure of the exit valve may be adjusted in a variety of ways. For example, the actuating pressure may be configured to continuously increase over time so that for each chest compression, the actuating pressure will be increased. Alternatively, the valve actuating pressure may be configured to incrementally increase over time. In this way, the actuating pressure will remain constant for a certain number of chest compressions and then will be increased for another set of chest compressions.

As with standard CPR, the methods of the invention may also include the steps of actively ventilating the person during the procedure. A variety of ventilating techniques may be utilized, including mouth to mouth, use of the ventilatory bag, automated ventilators, and the like.

Figure 9:
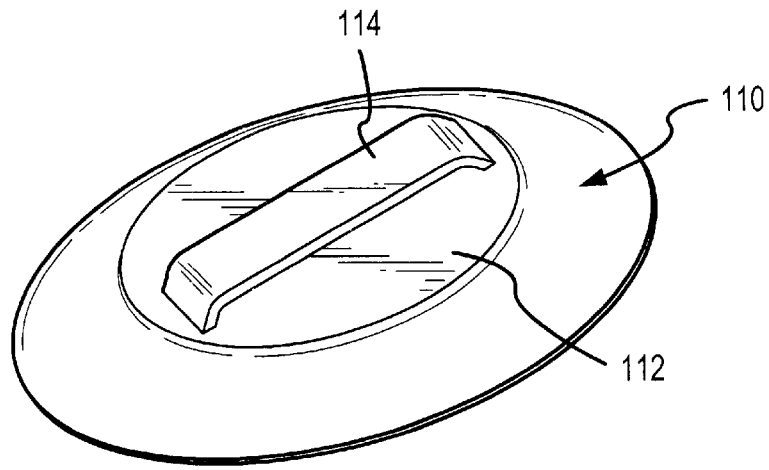
FIG. 9 is a top perspective view of a lifting member that may be employed to actively lift a person's chest.
Figure 10:
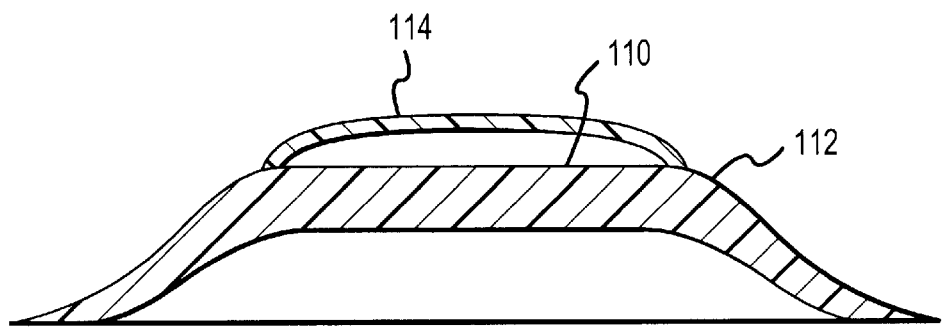
FIG. 10 is a cross-sectional side view of the lifting member of FIG. 9.

As previously mentioned, various techniques and/or equipment may be employed to actively compress or actively lift a person's chest. Merely by way of example, one such device is illustrated in FIGS. 9 and 10. As shown, a lifting device 110 may be used to actively lift a person's chest as well as to assist in performing chest compressions. Lifting device 110 comprises a body 112 that may be adhered by suction to the person's chest so that when a handle 114 is lifted, the person's chest will also be actively raised. It will be appreciated that the device of FIGS. 7 and 8 is merely one piece of equipment that may be utilized when performing CPR. A variety of other techniques may be used, including those described in U.S. Pat. No. 5,645,552, the complete disclosure of which is herein incorporated by reference.

Figure 11:
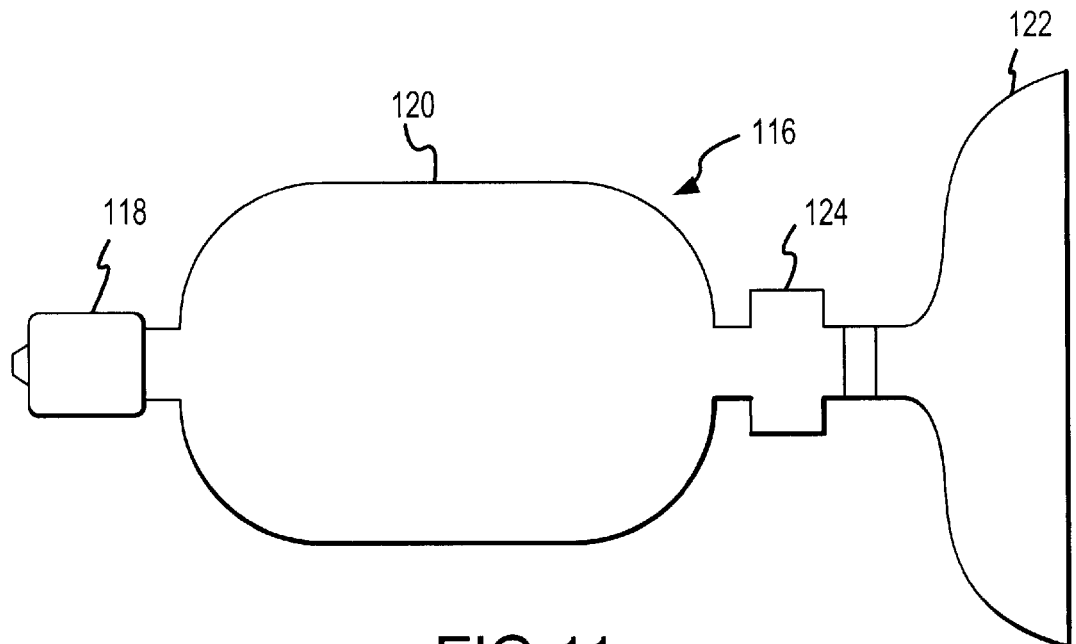
FIG. 11 is a schematic side view of a compressible bag having an exit valve with a variable actuating pressure according to the invention.

Referring now to FIG. 11, a ventilatory bag system 116 is shown. System 116 is illustrated to demonstrate one way in which an exit valve 118 having a variable actuating pressure may be incorporated into a piece of equipment that is to be interfaced with a person. However, it will be appreciated that the exit valves described herein may be incorporated into a variety of other types of equipment, or may even be used in a stand alone manner. Ventilatory system 116 further includes a compressible bag 120 which is coupled to a facial mask 122 that may be placed over a person's mouth and nose and sealed to the person's face when ventilating the person.

With this configuration, when expiratory gases are exhaled or forced out of a person, they proceed through facial mask 122 and into compressible bag 120. The expired gases exit system 116 through exit valve 118 after the actuating pressure of exit valve 118 has been met or exceeded. Exit valve 118 may be constructed in a manner similar to any of the embodiments described herein and may have the actuating pressure varied over time in a manner similar to that previously described.

Ventilatory system 116 may optionally include a threshold impedance valve 124 that prevents respiratory gases from entering into the person's airway until a threshold negative intrathoracic pressure is met or exceeded, at which time valve 124 opens to allow respiratory gases to enter into the patient's lungs in a manner similar to that described in connection with U.S. Pat. Nos. 5,551,420 and 5,692,498, previously incorporated by reference. Although exit valve 118 and threshold impedance valve 124 are shown as separate valves, it will be appreciated that in some cases exit valve 118 and threshold impedance valve 124 may be incorporated into the same valve structure.

Figure 12:
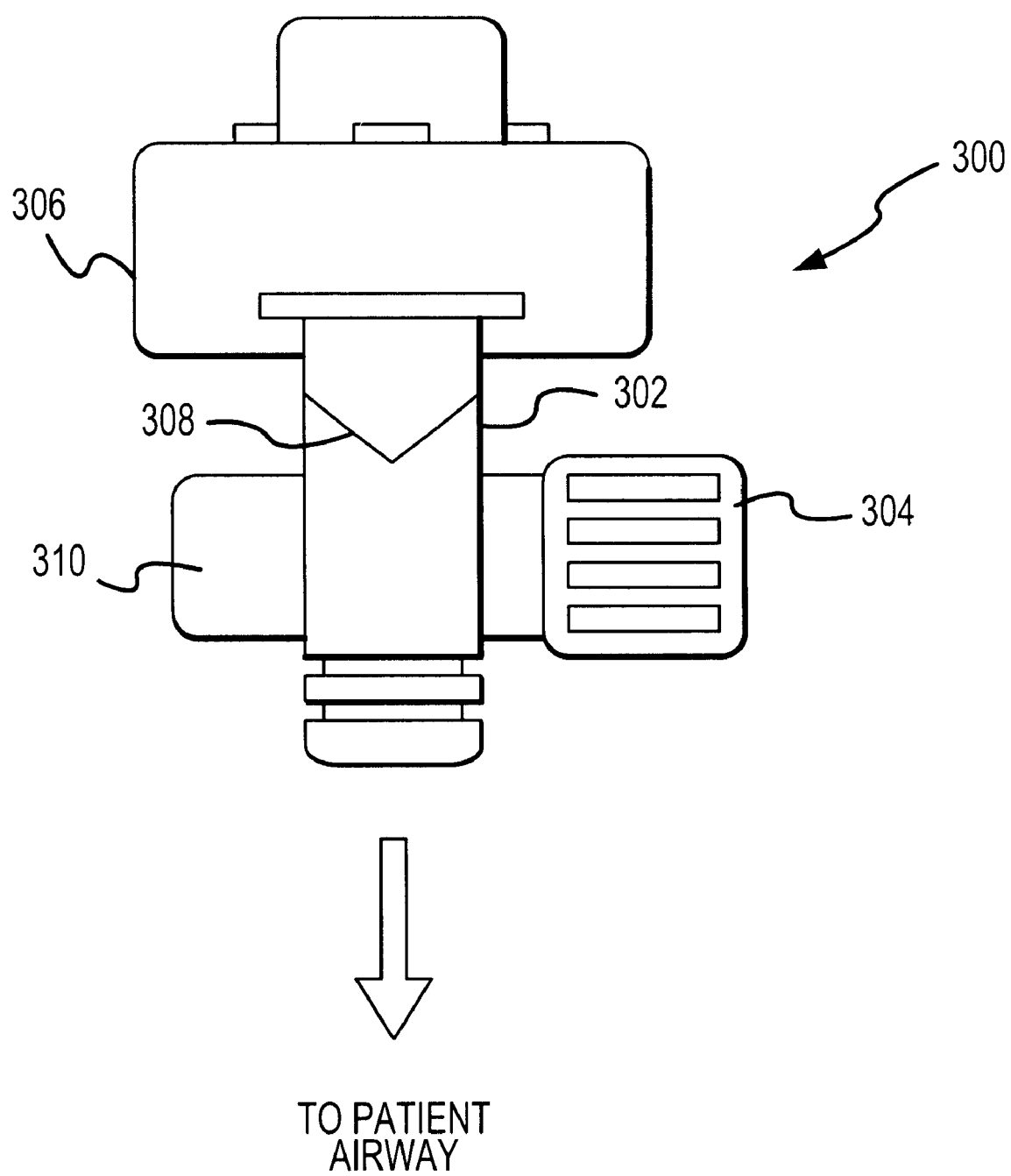
FIG. 12 is a schematic side view of one embodiment of a valve system having a variable actuating pressure and a negative pressure threshold valve according to the invention.

The exit or variable PEP valves as described herein may be incorporated into a valve system employing other types of valves. For examples, shown in FIG. 12 is a valve system 300 that comprises a housing 302 to which is coupled an exit valve 304. Exit valve 304 may be constructed similar to any of the exit of variable PEP valves described herein. Also coupled to housing 302 is an impedance threshold valve 306 that is employed to prevent respiratory gases from flowing to the patient's airway until a negative intrathoracic pressure is met or exceeded. In this way, the negative intrathoracic pressure within the patient may be augmented during the decompression step. Conveniently, valve 306 may be constructed similar to any of the threshold impedance valves described in U.S. Pat. Nos. 5,551,420 and 5,692,498, previously incorporated herein by reference.

Exit valve 304 is configured such that it is closed during compression of the patient's chest until the valve's actuating pressure is exceeded as previously described in connection with other embodiments. Conveniently, valve 304 may be opened during ventilation so that respiratory gases may be provided to the patient through valve 304. Further, a fishmouth valve 308 is disposed within housing 302 to direct compressed gases such that they exit through valve 304. Optionally, a check valve 310 may also be coupled to housing 302 to provide an additional access way to the patient airway.

The following are nonlimiting working examples where PEP was increased over time during various CPR procedures. It will be appreciated that the following invention is to be in no way limited to the following examples.

EXAMPLE ONE

In this example, standard (STD) cardiopulmonary resuscitation (CPR) was performed on pigs while increasing levels of positive expiratory pressure (PEP) and while periodically preventing the inflow of respiratory gases using an inspiratory threshold valve (ITV). The ITV valve used was an impedance threshold valve, commercially available from CPRx, Inc. and was set to open when the negative intrathoracic pressure exceeded about 20 cm $H_2O$. Nine pigs were used in the example, three of which were randomly assigned to receive STD CPR (without PEP) and the other six were randomly assigned to receive STD CPR plus the ITV (with increasing levels of PEP). After 4 minutes of cardiac arrest, each of the pigs received CPR for 28 minutes. At 12 minutes during CPR, PEP was applied at increasing levels of 2.5, 5.0, 7.5 and 10.0 cm $H_2O$ for four consecutive minutes each. Defibrillation was attempted after 28 minutes of CPR. The mean±SEM coronary artery perfusion pressure (diastolic aortic minus right atrial pressure) was measured at baseline and after increasing levels of PEP. The results for the STD CPR plus ITV group were 25±2, 26±2, 26±2, 26±2, and 25±3 mm Hg. For the STD CPR group, the results were 16±6, 13±6, 13±7, 12±6 and 12±6 mm Hg, where P<0.05 at 16, 20, 24 and 28 minutes. For the STD CPR+ITV group, all 6 pigs were successfully defibrillated. For the STD CPR group, one of the three pigs was successfully defibrillated. This example illustrates that by utilizing increasing levels of PEP during prolonged CPR, coronary perfusion pressure is maintained. The use of increasing PEP acts as an additional "pneumatic pump mechanism" during the compression phase of CPR.

EXAMPLE TWO

In this example, STD CPR with an ITV was performed in a porcine model of ventricular fibrillation. STD CPR and the configuration of the ITV was identical to Example One. Six samples were evaluated. After four minutes of cardiac arrest, STD CPR with the ITV was performed. After 8 minutes of performing STD CPR with the ITV and with intermittent positive pressure ventilation, increasing levels of PEP (2.5 and 5 cm $H_2O$) were applied sequentially for four minutes each. The amount of oxygenation before PEP was measured to be 125±25 torr, and at 2.5 and 5 cm $H_2O$ of PEP was measured to be 215±50 torr and 210±55 torr, respectively. For the last two measurements, P<0.03 vs. baseline before 2.5 cm $H_2O$ PEP and 5 cm $H_2O$ PEP. The coronary perfusion pressure before application of PEP was 25±2 mm Hg. The coronary perfusion pressure for PEP levels of 2.5 cm $H_2O$ and 5 cm $H_2O$ was 27±1 mm Hg and 27±2 mm Hg, respectively.

This example demonstrates that the use of increasing PEP in connection with an ITV significantly increased oxygenation and also increased coronary perfusion pressure. Hence, by increasing PEP over time, a "pneumatic pump" is created to both increase bronchiolar pressures leading to less atelectasis and by more efficient emptying of blood from the lungs each time the chest is compressed.

EXAMPLE THREE

This example is identical to Example Two except that the six porcine samples were treated with ACD CPR without the ITV. Before application of PEP, the oxygenation was 250±50 mm Hg. When applying PEP at 2.5 cm $H_2O$ and 5 cm $H_2O$, the oxygenation level was 220±45 and 180±50 mm Hg. The coronary perfusion pressure measured before application of PEP was 23±2 torr. After applying 2.5 cm $H_2O$ PEP and 5 cm $H_2O$ PEP, the coronary perfusion pressure was 28±3 torr and 30±4 torr, respectively. For the last two measurements, P<0.04 vs. baseline before 2.5 cm $H_2O$ and 5 cm $H_2O$ of PEP. This example illustrates that coronary perfusion pressure was increased when performing ACD CPR while increasing PEP.

EXAMPLE FOUR

In this example, ACD CPR was performed on pigs in the manner set forth in Example Three using an ITV configured in the manner specified in Example One. In the example, 16 pigs were used which were divided into 2 groups. All pigs received pressure controlled pure oxygen ventilation (pressure limit 60±5 cm $H_2O$) at a constant flow rate of 60 L/min, and a 5:1 compression—ventilation ratio. After 8 minutes of ACD CPR+ITV, the pigs were randomized into the two groups where one group received intermittent positive pressure ventilation (IPPV) alone, while the other group received increasing levels of continuous positive pressure ventilation (CPPV) with 2.5, 5.0, 7.5 and 10 cm $H_2O$ for four consecutive minutes each. Blood gases were assessed every four minutes. Defibrillation was attempted after 20 minutes of ACD CPR+ITV. The mean±SEM arterial $PO_2$ decreased from baseline in the IPPV group from 145±35 to 140±35, 120±25, 120±30, and 115±30 torr, but increased with PEP from 110±10 to 135±25, 155±30, 155±25 and 170±25 torr, respectively (P<0.05 at 5 PEP, and P<0.02 at 10 PEP for corresponding time points versus values at 12 minutes within groups). The mean ±SEM CPP (diastolic, aortic minus right atrial pressure) at baseline, and after increasing levels of PEP were 25±2, 27±2, 28±2, 28±3 and 27±3 mm Hg, versus 25±5, 29±6, 32±6, 32±6, and 28±5 mm Hg in the IPPV group, at corresponding time points respectively. Seven out of eight pigs in the PEP group and five out of eight pigs in the IPPV group were successfully defibrillated. This example illustrates that increasing levels of PEP during performance of ACD CPR with an ITV improves oxygenation and overall CPR efficiency. The example indicates that PEP may provide a pneumatic press like effect to enhance both oxygenation and blood transfer through the lungs during ACD CPR with the ITV.

The invention has now been described in detail for purposes of clarity of understanding. However, it will be appreciated that certain changes and modifications may be practiced within the scope of the appended claims.

What is claimed is:

1. A method for altering a person's ventilation, the method comprising:

interfacing an exit valve with a person's airway, wherein the exit valve is configured such that respiratory gases are prevented from exiting a person's lungs when the exit valve is closed and are permitted to exit a person's lungs when the exit valve is opened, and wherein the exit valve is configured to open when a valve actuating pressure is met or exceeded; and varying the valve actuating pressure over time.

2. A method as in claim 1, further comprising varying the valve actuating pressure within a range from about 0 cm $H_2O$ to about 20 cm $H_2O$.

3. A method as in claim 1, further comprising varying the valve actuating pressure over a time period in the range from about 5 minutes to about 30 minutes.

4. A method as in claim 1, further comprising periodically compressing a person's chest while the exit valve is interfaced with a person's airway.

5. A method as in claim 4, further comprising compressing a person's chest with a compression mechanism.

6. A method as in claim 4, further comprising periodically compressing a person's abdomen in an alternating manner with chest compressions.

7. A method as in claim 4, further comprising periodically actively lifting a person's chest in an alternating manner with chest compression.

8. A method as in claim 7, further comprising interfacing an impedance valve with a person's airway, wherein the impedance valve is configured to open to permit respiratory gases to flow into a person's lungs once a threshold negative intrathoracic pressure is met or exceeded.

9. A method for performing cardiopulmonary resuscitation, the method comprising:

periodically compressing a patient's chest;

preventing respiratory gases from exiting a patient's lungs during the compression step with an exit valve that is interfaced with a patient's airway until an actuating pressure of the exit valve is met or exceed, at which time the exit valve opens to permit respiratory gases from exiting a patient's lungs; and varying the actuating pressure of the exit valve over time.

10. A method as in claim 9, further comprising varying the valve actuating pressure within a range from about 0 cm $H_2O$ to about 20 cm $H_2O$.

11. A method as in claim 9, further comprising varying the valve actuating pressure over a time period in the range from about 5 minutes to about 30 minutes.

12. A method as in claim 9, further comprising compressing a person's chest with a compression mechanism.

13. A method as in claim 12, further comprising periodically actively lifting a person's chest in an alternating manner with chest compression.

14. A method as in claim 13, further comprising interfacing an impedance valve with a person's airway, wherein the impedance valve is configured to open to permit respiratory gases to flow to a person's lungs once a threshold negative intrathoracic pressure is met or exceeded.

15. A method as in claim 9, further comprising periodically compressing a patient's abdomen in an alternating manner with chest compressions.

16. A method as in claim 9, further comprising increasing the actuating pressure over time.

* * * * *